(12) United States Patent
Kaneko et al.

(10) Patent No.: US 7,856,340 B2
(45) Date of Patent: Dec. 21, 2010

(54) MULTI-FUNCTIONAL SENSOR AND METHOD OF SENSING

(75) Inventors: Norio Kaneko, Atsugi (JP); Takehiko Kawasaki, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 75 days.

(21) Appl. No.: 12/377,377

(22) PCT Filed: Oct. 10, 2007

(86) PCT No.: PCT/JP2007/070211
§ 371 (c)(1),
(2), (4) Date: Feb. 12, 2009

(87) PCT Pub. No.: WO2008/047813
PCT Pub. Date: Apr. 24, 2008

(65) Prior Publication Data
US 2010/0217539 A1  Aug. 26, 2010

(30) Foreign Application Priority Data
Oct. 12, 2006  (JP) .............................. 2006-278919
Sep. 5, 2007  (JP) .............................. 2007-230405

(51) Int. Cl.
*G01D 1/18* (2006.01)
*G01N 3/00* (2006.01)

(52) U.S. Cl. ........................ 702/179; 702/33; 702/41; 702/42; 702/43; 702/44; 702/104; 702/116; 702/189; 702/190; 702/193; 702/199; 358/1.12; 358/3.24; 358/504; 358/406; 358/296; 358/498; 73/1.12; 73/12.09; 73/12.11; 73/12.12; 73/12.13; 73/159; 347/105; 347/106; 347/153; 347/155; 347/158; 347/262; 347/264; 399/45; 271/258.01; 271/262

(58) Field of Classification Search .................... 702/33, 702/41, 42, 43, 44, 104, 116, 179, 189, 190, 702/193, 199; 358/3.24, 504, 406, 296, 498; 73/12.01, 12.09, 12.11, 12.12, 12.13, 159; 347/105, 106, 153, 155, 158, 262, 264; 399/45; 271/258.01, 262
See application file for complete search history.

(56) References Cited

U.S. PATENT DOCUMENTS 5,104,488 A  4/1992  Chase .......................... 162/198
(Continued)

FOREIGN PATENT DOCUMENTS

| CN | 1401498 | 3/2003 |
|----|---------|--------|
| CN | 1732378 | 2/2006 |
| WO | 2004/060781 | 7/2004 |

OTHER PUBLICATIONS

J. Engel, et al., "Sensors and Actuators", A117, vol. 50 (2005).
(Continued)

*Primary Examiner*—Sujoy K Kundu
(74) *Attorney, Agent, or Firm*—Fitzpatrick, Cella, Harper & Scinto

(57) ABSTRACT

A multi-functional sensor for deriving information on a recording sheet material comprising an impact-applying unit for applying an external mechanical force onto the recording sheet material, a signal-detecting unit for detecting a signal of response of the recording sheet material to the external mechanical force, a signal-processing unit for processing the signal, and a signal-judging unit for deriving a property of the recording sheet material by comparison of a signal from the signal-detecting unit or the signal processing unit with information memorized preliminarily, wherein the signal-processing unit comprises a separation section for separating the signal from the signal-detecting unit into output signals on the properties of the recording sheet material, and a processing section for deriving, by statistical treatment, a correlation equation showing a correlation between the separated output signal and the properties of the recording sheet material.

5 Claims, 10 Drawing Sheets

U.S. PATENT DOCUMENTS

| | | | | |
|---|---|---|---|---|
| 5,574,279 | A | 11/1996 | Ikeda et al. | 250/306 |
| 7,239,817 | B2 * | 7/2007 | Kaneko et al. | 399/45 |
| 7,583,413 | B2 * | 9/2009 | Nojiri et al. | 358/3.24 |
| 2003/0053090 | A1 | 3/2003 | Nojiri et al. | |
| 2005/0271403 | A1 | 12/2005 | Kaneko et al. | 399/44 |
| 2006/0276946 | A1 | 12/2006 | Kaneko et al. | 701/45 |

PUBLICATIONS

Enomae Toshiharu, "Nippon Gazoh Gakkai-shi", Journal of Image Technology Society of Japan, vol. 43, No. 4, pp. 276 (2004).

International Search Report and Written Opinion dated Mar. 28, 2008 in counterpart PCT/JP2007/070211.

J. Engel, et al., "Polymer Micromachined Multimodal Tactile Sensors", Sensors and Actuators, A117, pp. 50-61 (2005).

Enomae Toshiharu, "Nippon Gazoh Gakkai-shi", Journal of Imaging Society of Japan, vol. 43, No. 4, pp. 276 (2004).

English-language translation of Enomae Toshiharu, "Nippon Gazoh Gakkai-shi", Journal of Imaging Society of Japan, vol. 43, No. 4, pp. 276 (2004).

Chinese Office Action dated Apr. 22, 2010 issued during prosecution of corresponding Chinese Patent Application no. 200780037965.6.

* cited by examiner

MULTI-FUNCTIONAL SENSOR AND METHOD OF SENSING

TECHNICAL FIELD

The present invention relates to a sensor for sensing a state or phenomenon resulting from combination of plural properties and characteristics of a material.

The present invention relates also to a method for sensing mechanical characteristics, mechanical properties, a surface state, an internal structure, and related properties of a viscoelastic sheet material like information-recording sheets constituted of an organic material, an inorganic material, a mixture, or a laminate thereof; phenomena and states thereof.

BACKGROUND ART

Conventionally a sensor determines a specific physical quantity. For determining a phenomenon or a state, plural physical quantities are measured separately, and the measurement results are collectively analyzed. For example, a property of a material detectable by touch feeling, such as hardness and a temperature, can be sensed by use of a combination of miniaturized sensors, as described in a document: J. Engel et al., Sensors and Actuators, A117, 50 (2005).

In recording with an ink-jet printer or a copying machine, various information-recording paper sheet materials (hereinafter referred to simply as "recording sheets"). The recording sheets are viscoelastic. For image formation, physical properties or a state of the recording sheet should be detected for setting the optimum image formation conditions. The information on the recording sheet includes thickness, roughness, density, rigidity, moisture content, electric resistivity, temperature, sizing, kind of paper (paper category such as plain paper, rough paper, gloss paper, and coated paper, and paper model number), and so forth. The kind and category of the paper are not properties but a state of the recording sheet. The paper-type number is an identification number given by the paper maker. The properties and the states of the recording sheet are not uniformly reflected to image formation conditions. For example, in electrophotographic copying, for delivery of a recording sheet, paper sheet thickness, sheet rigidity, and sheet deformability are important, whereas in the processes of image development, image transfer, and image fixation, surface resistivity, moisture content, roughness, gloss, and the kind of paper are important. The methods of determination of properties and states of the paper sheet such as thickness and density are standardized by Japanese Industrial Standard (JIS), and described also in the document: "ENOMAE Toshiharu: Nippon Gazoh Gakkai-shi (Journal of Image Technology Society of Japan) vol. 43, (No. 4), 276 (2004)".

DISCLOSURE OF THE INVENTION

The method of determining the properties or states of the recording sheets are standardized as mentioned above. Generally, the recording sheet is a mass of vegetable fibers constituted mainly of cellulose, and the cellulose or vegetable fibers are known to be bonded by hydrogen bonding between the fibers to form a network. The state of this hydrogen-bonding network changes irreversibly by the temperature or the humidity. Therefore, the properties of recording sheets of the same specification are affected irreversibly by storage conditions and recording conditions. The specification of the properties of the paper sheet given by a paper maker is merely a rough indicator. In use of various recording sheets in image formation, the properties of the recording sheets in the image formation in a copying machine should be estimated. However, incorporation of plural sensors in the copying machine for measuring the properties will complicate the machine design, raise the machine cost owing to increased number of sensors, and make the machine control complicated.

For measurement of the properties inside a copying machine or a printer, plural measurement means are necessarily incorporated in the apparatus. The test devices designated in Japanese Industrial Standard for the above measurements, such as a paper sheet thickness tester and a Gurley stiffness tester, occupy respectively a setting area of about 30 cm×30 cm and are expensive. For measurement of plural properties, plural measurement means are necessary.

With combination of miniature sensors, individual properties are measured separately and the measurement results are analyzed by an algorithm to estimate the state and phenomenon as well as the properties of the measurement object. In this case, however, different kinds of sensors should be incorporated in a small space. Therefore the construction is complicated and the analysis of the output signals from the sensors is complicated. Furthermore, depending on the property to be measured, the individual sensors can not be incorporated in a desired small space owing to wiring design problems and interference between the sensors.

The present invention intends to provide a small-sized inexpensive sensor (multi-functional sensor) for measurement of plural properties and characteristics of a recording sheet, and to provide a method for measurement thereof. The signals output from the sensor contain information on plural kinds of properties and characteristics of the measurement object. The objective information is derived by statistic regression analysis of the plural pieces of the information. Since plural kinds of information are coexisting, not only the intended property but also the state of the measurement object can be estimated therefrom.

Accordingly, in image formation with a copying machine, information on properties and characteristics important in the steps of image fixation and image transfer can be estimated with a single sensor without employing plural sensors respectively for individual properties.

The present invention is directed to a multi-functional sensor for deriving information on a recording sheet material comprising an impact-applying unit for applying an external mechanical force onto the recording sheet material, a signal-detecting unit for detecting a signal of response of the recording sheet material to the external mechanical force, a signal-processing unit for processing the signal, and a signal-judging unit for deriving a property of the recording sheet material by comparison of a signal from the signal-detecting unit or the signal processing unit with information memorized preliminarily; wherein the signal-processing unit comprises a separation section for separating the signal from the signal-detecting unit into output signals on the properties of the recording sheet material, and a processing section for deriving, by statistical treatment, a correlation equation showing a correlation between the separated output signal and the properties of the recording sheet material.

The correlation equation can be derived preliminarily by regression analysis of results of measurement of the properties of the recording sheet material.

The present invention is directed to a method of detection of a state or phenomenon caused by combination of properties of a recording sheet material, comprising the steps of: separating an output signal from a sensor into information on the properties, and deriving the property of the recording sheet material based on a correlation equation derived preliminarily by statistical processing on correlation between the separated output signal and the property of the recording sheet material.

The correlation equation can be derived preliminarily by regression analysis of results of measurement of properties of the recording sheet material.

The property of the recording sheet material to be measured can be at least one selected from the group consisting of mechanical properties, elastic properties, viscoelastic properties, properties relating to an interface and internal structure.

The properties to be measured by the present invention include properties and characteristics of a sheet material, or properties correlated therewith, including mechanical properties, elastic properties, viscoelastic properties, interface properties, and internal structural properties.

The mechanical properties of the sheet material include stiffness such as Gurley stiffness and Clerk stiffness, hardness, tensile strength, and compression deformation.

The elastic properties and viscoelastic properties include Young's modulus. When the Young's modulus Y is represented by a complex notation (Y=Y1+iY2), the elastic property is represented by the real number component Y1, and the viscoelastic property is represented by two values of the imaginary number component and the loss factor tan $\delta$=Y2/Y1. Thus the real number component of the Young's modulus represents the elastic property and the imaginary number component thereof and the loss factor represents the viscoelastic property.

The interface properties include surface roughness of the sheet material, a moisture content on the sheet material surface or at the layer interface of multi-layered sheet material, the amount of the toner (toner thickness, and gradation) transferred and fixed by electrophotography.

The internal structural properties include a density, a basis weight, and a sheet thickness.

Further features of the present invention will become apparent from the following description of exemplary embodiments with reference to the attached drawings.

BEST MODES FOR CARRYING OUT THE INVENTION

Figure 1A:
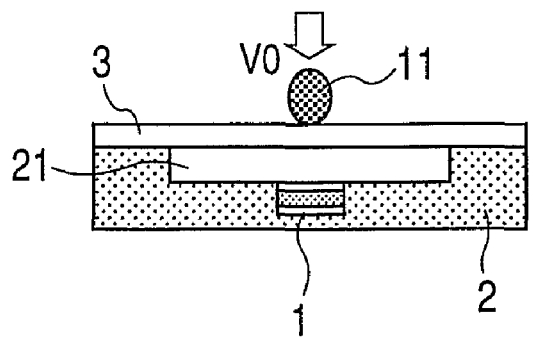
FIGS. 1A, 1B, and 1C illustrate the principle of the present invention.
Figure 1B:
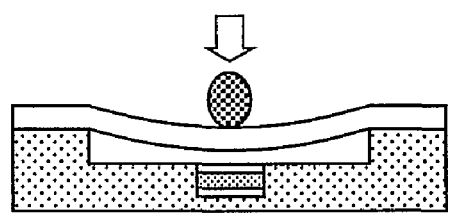
Figure 1C:
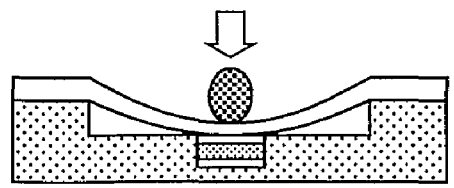

FIGS. 1A, 1B, and 1C illustrate the principle of the present invention. In this example, measurement object 3 is a sheet material like a recording sheet. The sensor (multi-functional sensor) of the present invention has a force-applying means for applying an external force to measurement object 3, and a pressure sensor 1 fixed to sheet support 2 for detecting a response of the measurement object to the applied external force. In FIGS. 1A, 1B, and 1C, the external force-applying means is rigid body 11 having mass m, and the rigid body is allowed to collide at a velocity $V_0$ against the measurement object by free falling. Sheet support 2 has concave 21. On collision of the rigid body against measurement object 3 as illustrated in FIG. 1A, the measurement object is deformed as illustrated in FIG. 1B, and is pressed against pressure sensor 1 placed in the concave as illustrated in FIG. 1C. At this moment, pressure sensor 1 outputs a signal. That is, the velocity of the rigid body is decreased by the deformation of measurement object 3: the rigid body presses the measurement object 3 against the concave bottom until the velocity of the falling rigid body becomes zero. Before contact of the measurement object, the pressure sensor 1 outputs no signal. On the contact of the measurement object with the sensor, the measurement object 3 is deformed by pressing and the velocity of the rigid body is decreased. Therefore, the output of the pressure sensor contains plural pieces of information regarding the deformation and compression of the measurement object.

The method of the external force application is not limited to the aforementioned free falling. The external force may be applied by a spring, a magnetic force, an electrostatic force, and so forth. The impact-applying member (external force-applying means) may be selected to meet the purpose without limitation in the number or arrangement of the means. As the pressure sensor, a piezo-element is useful, but is not limited thereto in the kind and shape thereof. In FIGS. 1A, 1B, and 1C, the impact-applying member and the pressure sensor are separated, but may be integrated, and the number of the impact-applying members may be different from the number of the pressure sensors. Further, the impact-applying member and the pressure sensor are confronted with each other with interposition of the measurement object in FIGS. 1A, 1B, and 1C, but the arrangement is not limited thereto.

Figure 2:
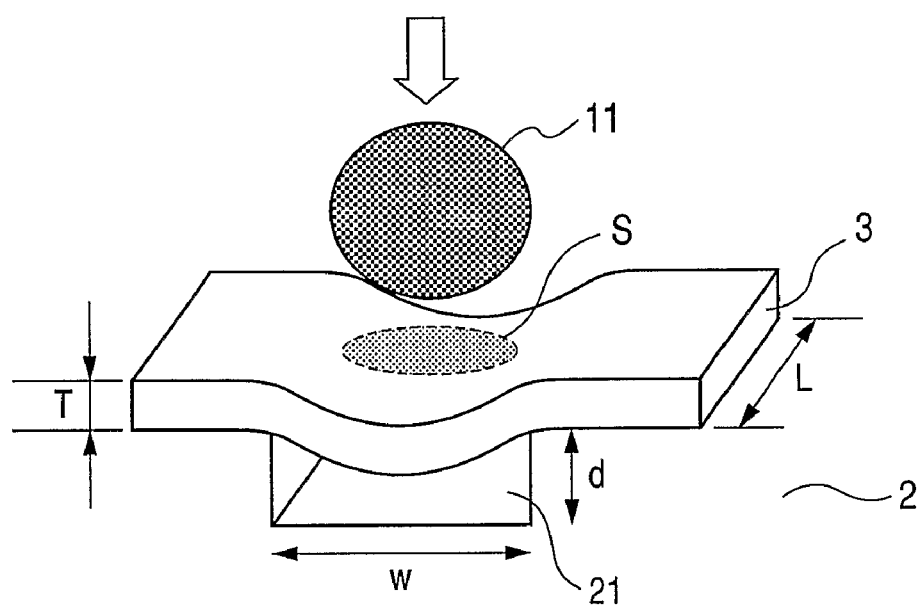
FIG. 2 illustrates the factors contributing to the signals in the present invention.

FIG. 2 illustrates the factors contributing to the output signals from the sensor in the present invention. The mechanical factors contributing to the output include depth d, width w, and the front-to-back length of concave 21; area S of contact of impact-applying rigid body 11 with measurement object 3; elastic modulus k of the pressure sensor (omitted in FIG. 2); and mass m and collision velocity $V_o$ of the rigid body. The factors of the measurement object contributing to the output, in the case of a recording sheet, include paper thickness T, effective deformation breadth L of the paper sheet, density, Young's modulus, stiffness, flatness, smoothness, and moisture content of the recording paper sheet; and their change caused by environmental hysteresis and handling history. For the measurement object other than the recording sheet, the factors can be different from the above.

Of the above factors, mechanical and structural factors can be treated as the constants after determination of the construction. After determination of the construction, the output signal in the measurement reflects the factors relating to the measurement object such as the thickness, the density, and the Young's modulus, and environment of the measurement object.

Figure 10:
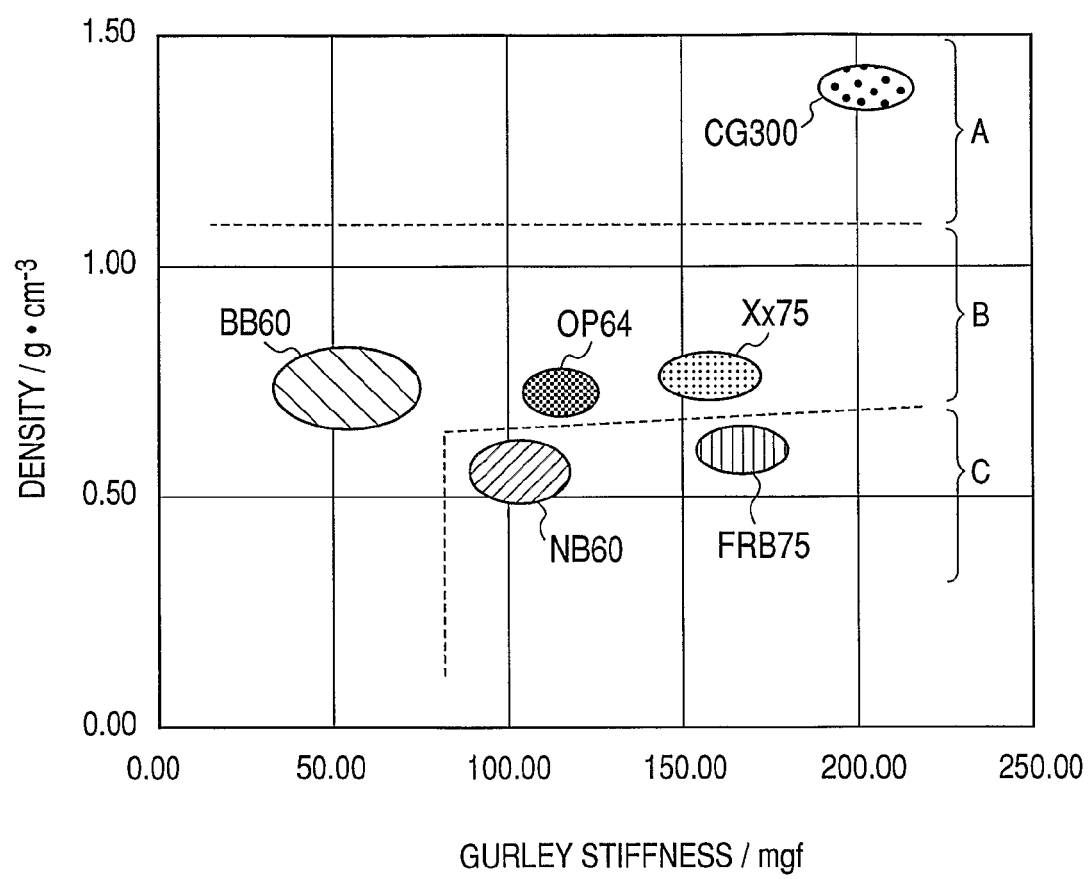
FIG. 10 illustrates the standards for estimation in the present invention.

The concave illustrated in FIGS. 1A, 1B, and 10 is not essential. Obviously, the compression only can give signal output from the pressure sensor regarding the properties of the measurement object such as the thickness, density and Young's modulus. When the impact-applying member and the pressure sensor are integrated or placed on the same side of the measurement object, the compression is not necessary.

Figure 3:
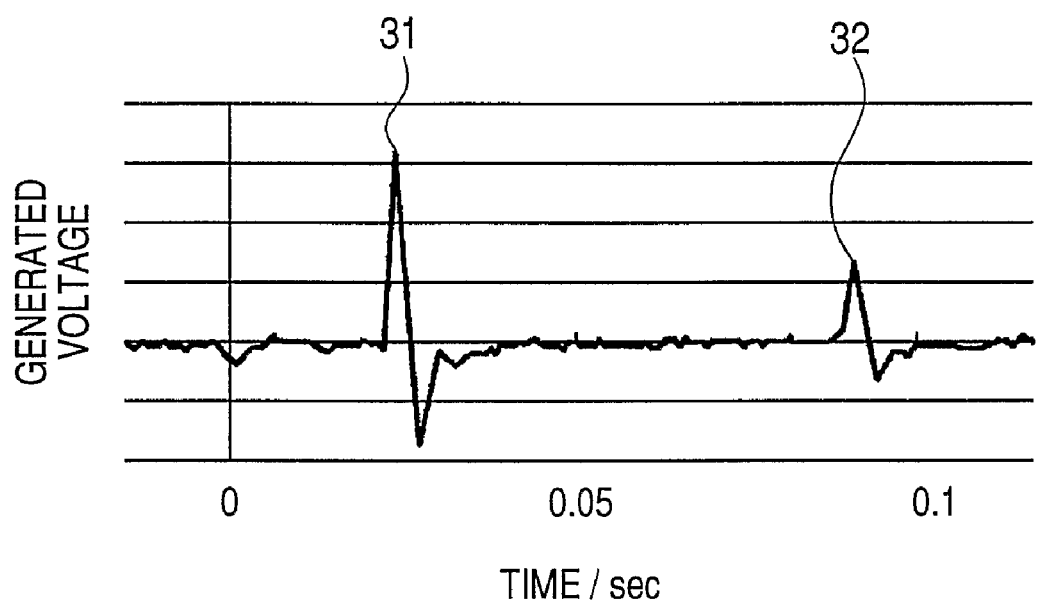
FIG. 3 illustrates an example of output from the sensor in the present invention.

FIG. 3 illustrates an example of output from the sensor. In FIG. 3, the impact is applied twice by changing the impact velocities: a strong impact at a higher velocity, and weak impact at a lower velocity. The signal from the sensor is not limited to the generated voltage, but may be a half width of the voltage peak, a gradient of the voltage curve, frequency dependence, area, and so forth. When the impact-applying member is allowed to fall freely, the impact-applying means can collide two or more times by repulsion by the measurement object. In such a case the signal may be a number of the collisions within a predetermined time length, or a time length for predetermined number of the impacts.

The intensity of the external force, the number and cycle of the external force application are not limited insofar as the measurement object is not deteriorated in the quality. The material of the sensor is not limited. The type of the sensor for pressure detection is not limited. The pressure may be directly measured, or the change of the velocity of the impact-applying member by collision may be measured instead of the pressure measurement. The system, material, and member may be selected to meet the use of the sheet material. The number of the impact-applying units and the number of the signal-detecting units need not be the same. Plural signal-detecting units may be employed for one impact-applying unit, or plural impact-applying units may be employed for one signal-detecting unit. Such constitutions may be combined.

Figure 4:
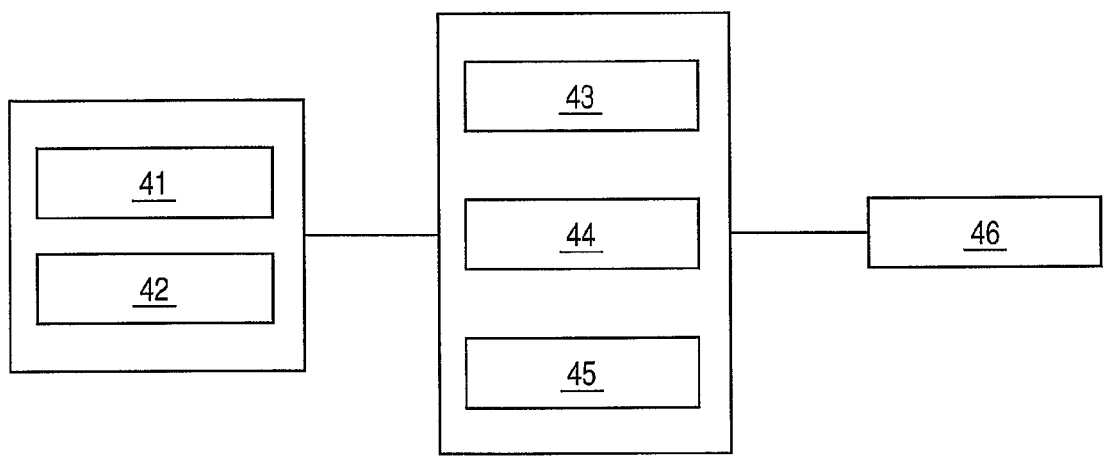
FIG. 4 illustrates a constitution of the present invention.

FIG. 4 illustrates a constitution of the sensor of the present invention. The impact-applying unit serves to apply an external force to a measurement object. The signal-detecting unit detects a response to the external force applied to the measurement object. The signal detected by the signal-detecting unit is transmitted as an output signal to the signal-processing unit or the signal-judging unit. The signal-processing unit has two functional sections. The first of the functional sections processes the output signals: for example, removal of noises, separation of necessary signal component such as intensity, amplitude, and phase of the signal; and transmits the results to the signal-judging unit. The second of the two functional sections processes statistically (e.g., by regression analysis) the results of processing by the above first functional section. The information separated and treated by the above two functions is memorized in the information memory unit.

The signal-judging unit compares the signal components separated from the signal-processing unit with information memorized in the information memory unit, and judges the properties and state of the measurement object. The judgment results can be displayed on display unit as necessary, and can be transmitted via the Internet.

A method of treatment of signals by the signal-processing unit, signal-separating section, signal-judging unit, information memory unit, and display unit is described by taking an electrophotographic recording sheet as an example. In this description, the type number and category an unknown paper sheet are identified based on the thickness, rigidity, and density of the paper sheet as the characteristics of the recording sheet.

For the above purpose, the correlation of the sensor output with the properties and characteristics of the recording sheet is checked to confirm the reliability of the measurement in the present invention. A personal computer employing Windows® 2000 of Microsoft Corporation as OS is used as the signal-processing unit, signal-separating section, signal-judging unit, information memory unit, and display unit. Excel® (spreadsheet software) of Microsoft Corporation is used for the statistical treatment. For comparison, the thickness and stiffness of the paper sheet are measured by a paper thickness tester (Kumagaya Riki Kogyo K.K.: TM600) and an automatic Gurley stiffness tester (Kumagaya Riki Kogyo K.K.), respectively based on JIS standard. The density of the paper sheet is calculated from the basis weight measured by weighing the A4-size paper sheet by an electronic balance and the paper sheet thickness measured by paper thickness tester TM600, as described by ENOMAE Toshiharu: Nippon Gazoh Gakkai-shi (Journal of Image Technology Society of Japan) vol. 43, (No. 4), 276 (2004), (P277).

The signal-processing unit conducts the processing, for example, as follows with plural recording sheets. Multiple regression equations (1) and (2) are assumed regarding the paper sheet thickness t (mm), the paper sheet density $\rho$ (g/cm$^3$), the voltage $V_1$ (V) generated at the impact velocity of $v_1$ (m/sec), and the voltage $V_2$ (V) generated at the impact velocity of $v_2$ (m/sec):

$$t = aV_1 - bV_2 + c \quad (1)$$

$$\rho = dV_1 - eV_2 + f \quad (2)$$

The constants a, b, c, d, e, and f are determined by a least square method by utilizing the function of the aforementioned Excel. The multiple regression equations show the influence of the variance of plural explanatory variables on plural objective variables. For the objective variables of the paper sheet thickness and the paper density, the multiple regression equations can be obtained by taking actual measurement values at two or more impacts.

According to the above multiple regression equations, information on the sheet thickness and density of an unknown paper sheet can be obtained from the two generated voltages. Further, information which cannot be represented by physical quantities such as a paper-type number and a category of an unknown paper sheet can be obtained by utilizing a graph of the above values plotted on the coordinate, or utilizing a cause-effect relation of other physical quantities. The Gurley stiffness can be treated in a similar manner. The combinations of the density and the Gurley stiffness; the paper thickness and the Gurley stiffness; and the density, the paper sheet thickness, and Gurley stiffness can be treated by multiple regression equations.

The multiple regression equations are not limited to the linear equation described above, or the information treated is not limited to be the two kinds. The type of the multiple regression equations and the number of the variables may be set to meet the purpose. The correlation coefficients of the regression equations may be limited as desired. Plural regression equations may be derived and may be estimated with weighting.

The measurement results obtained by the measurement methods specified by JIS standard are compared with the calculation results obtained from the above regression equations to confirm whether or not the calculation results coincide satisfactorily with the measurement results.

After confirmation of the reliability of the calculation results, the multiple regression equations are memorized in the information memory unit. The multiple regression equations may be derived and confirmed immediately before the measurement of an unknown paper sheet. Otherwise, the multiple regression equations may be derived preliminarily with the same or another sensor and this information may be memorized in the information memory unit.

Then an unknown measurement object is subjected to the measurement. The signal-judging unit calculates the intended property or characteristic, or estimates the paper type number, the paper category, and the entire shape. The results of the judgment may be displayed in the display unit or may be transmitted via the Internet if necessary. The signal-processing unit or the signal-judging unit may be constituted of a commercial personal computer, or constituted of a single-purpose micro-computer. The signal may be judged by comparison with information memorized in a device other than that of the present invention.

The display unit shown in FIG. 4 is not essential in the sensor of the present invention. For example, in a copying machine, the display unit may be omitted, and the conditions for sheet delivery, image transfer, fixation, and so forth may be controlled by reference to the sensor measurement results.

The measurement area of the measurement object, namely the area of collision in FIG. 2, is not limited. The measurement may be conducted in an atom-size area, or in an area of several square millimeters or several square meters to meet the intended end usage. For evaluation of a minute region of the sheet material, the collision is caused in a small area, whereas for evaluation of an average properties and characteristics, the collision is caused in a larger area.

EXAMPLES

The present invention is described below more specifically with reference to Examples.

Example 1

Figure 5:
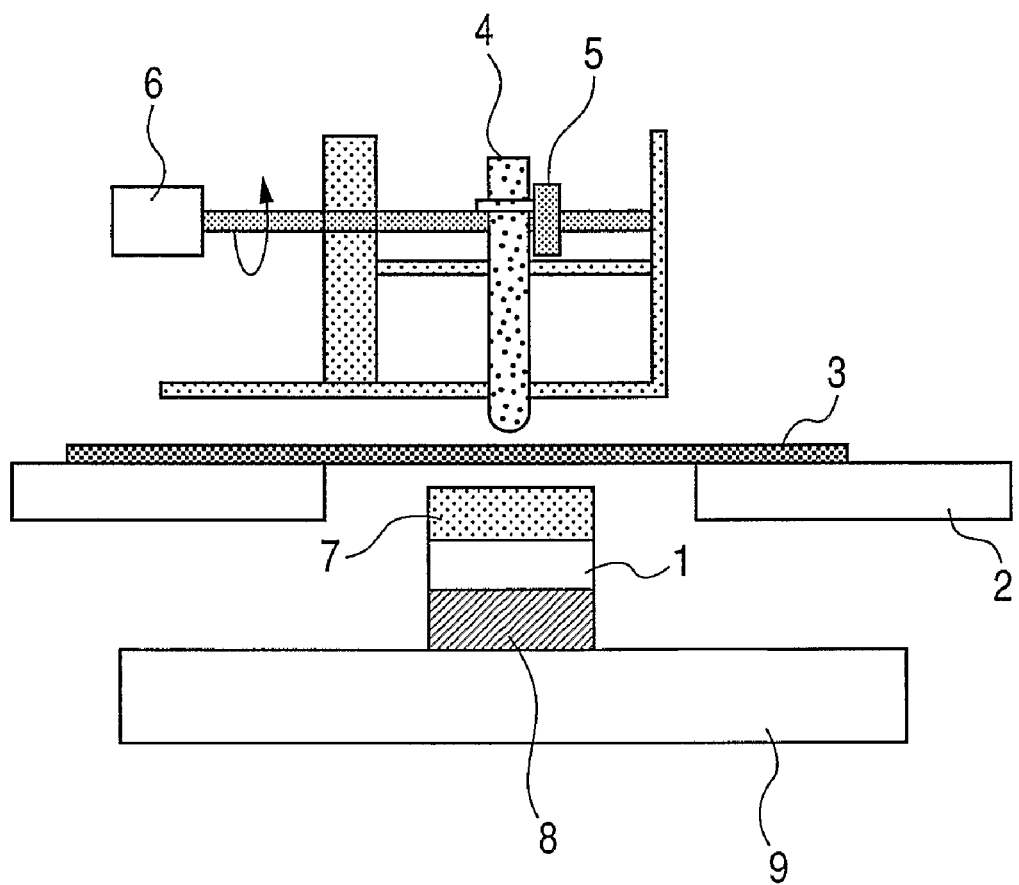
FIG. 5 illustrates schematically a principle of a constitution of the present invention.

FIG. 5 illustrates schematically a constitution of the present invention. In FIG. 5, driving force-producing device 6 rotates cam 5 to cause free falling of impact-applying member 4 to apply an external force to measurement object 3. Impact-applying member 4 which has collided against measurement object 3 can be repelled and collide repeatedly against the measurement object. However, in this Example, the impact-applying member is pulled up after the one impact. Sheet support 2 for supporting the measurement object has its upper face higher than the upper face of impact-receiving member 7 by a level difference of 0.25 mm. Impact-receiving member 7 serves to protect pressure sensor 1 as well as to transmit the external force applied by impact-applying member 4 to pressure sensor 1. Connecting member 8 connects pressure sensor 1 to fixation table 9.

Impact-applying member 4 is made of stainless steel, having a weight of 4 g, a diameter of 3.5 mm, and a tip curvature of 100 mm diameter. Cam 5 is designed to apply external force at 0.48 m/s and 0.24 m/s twice successively within 0.2 second. A piezo-element is employed as pressure sensor 1.

As the measurement objects, were used electrophotographic recording sheets (OHT CG3300 of Canon K.K.; Office Planner OP64; Bajar Bond BB60; Zerox Xx75; Neena Bond NB60; and Fox River Bond FRB75). With the recording sheets, the multiple regression equations were derived by use of Excel® (spreadsheet software) of Microsoft Corporation installed in a personal computer containing an OS of Windows® 2000 of Microsoft Corporation. For comparison, the paper sheet thickness was measured by a paper thickness tester (Kumagaya Riki Kogyo K.K.: TM600) specified by JIS standard. The density of the paper sheet was calculated from the basis weight measured by weighing the A4-size paper sheet by an electronic balance and the paper sheet thickness measured by paper thickness tester TM600, as described by ENOMAE Toshiharu: Nippon Gazoh Gakkai-shi (Journal of Image Technology Society of Japan), vol. 43, (No. 4), 276 (2004), (P277).

FIG. 3 illustrates an example of the output from the piezo-electric element in measurement with a Zerox Xx75 paper sheet. In FIG. 3, peak 31 indicates the generated voltage by external force application at a rate of 0.48 m/s, and peak 32 indicates the one at a rate of 0.24 m/s. With 10 sheets respectively of the above-mentioned six kinds of the recording sheets, thirty measurements were conducted with each recording paper sheet at different measurement positions. From the results, the paper sheet thickness t (mm), the paper sheet density $\rho$ (g/cm$^3$), the generated voltage $V_1$ (V) at the impact velocity of 0.48 m/s, and the generated voltage $V_2$ (V) at the impact velocity of 0.24 m/s were statistically processed by the information-processing unit. As the results, the multiple regression equations below were derived. The correlation coefficients were respectively not less than 0.98 for the both multiple regression equations.

$$t=1.05\times10^{-3}V_1-3.33\times10^{-2}V_2+0.127 \quad (3)$$

$$\rho=0.150V_1-0.132V_2+0.304 \quad (4)$$

Figure 6:
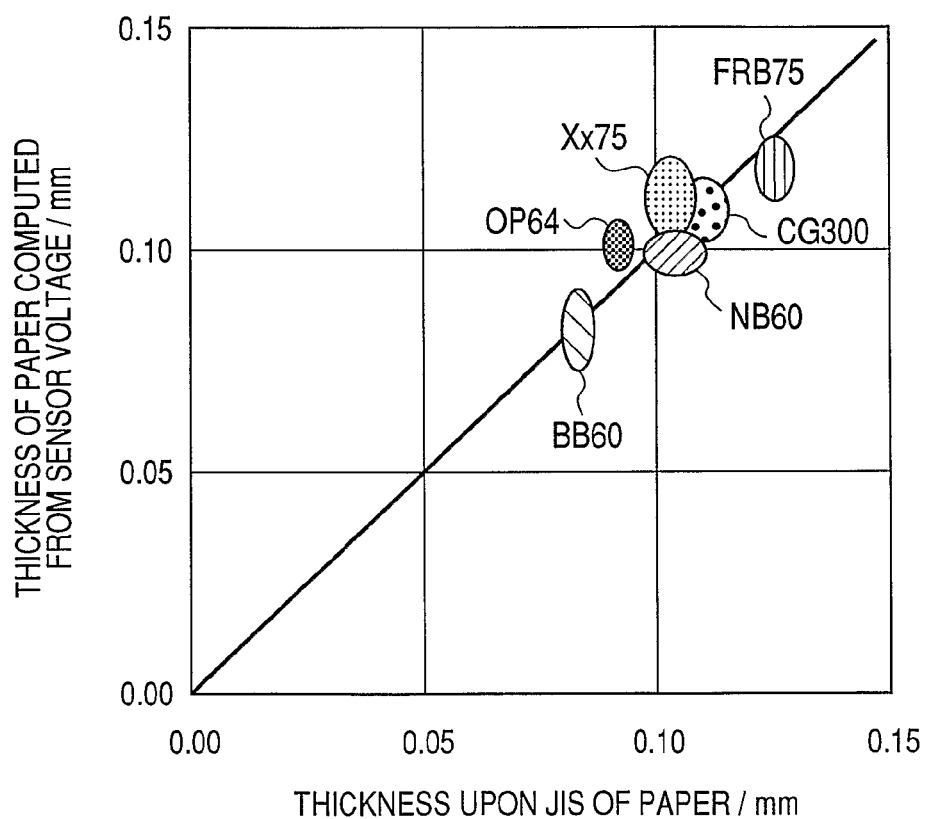
FIG. 6 illustrates the results of measurement in the present invention.
Figure 7:
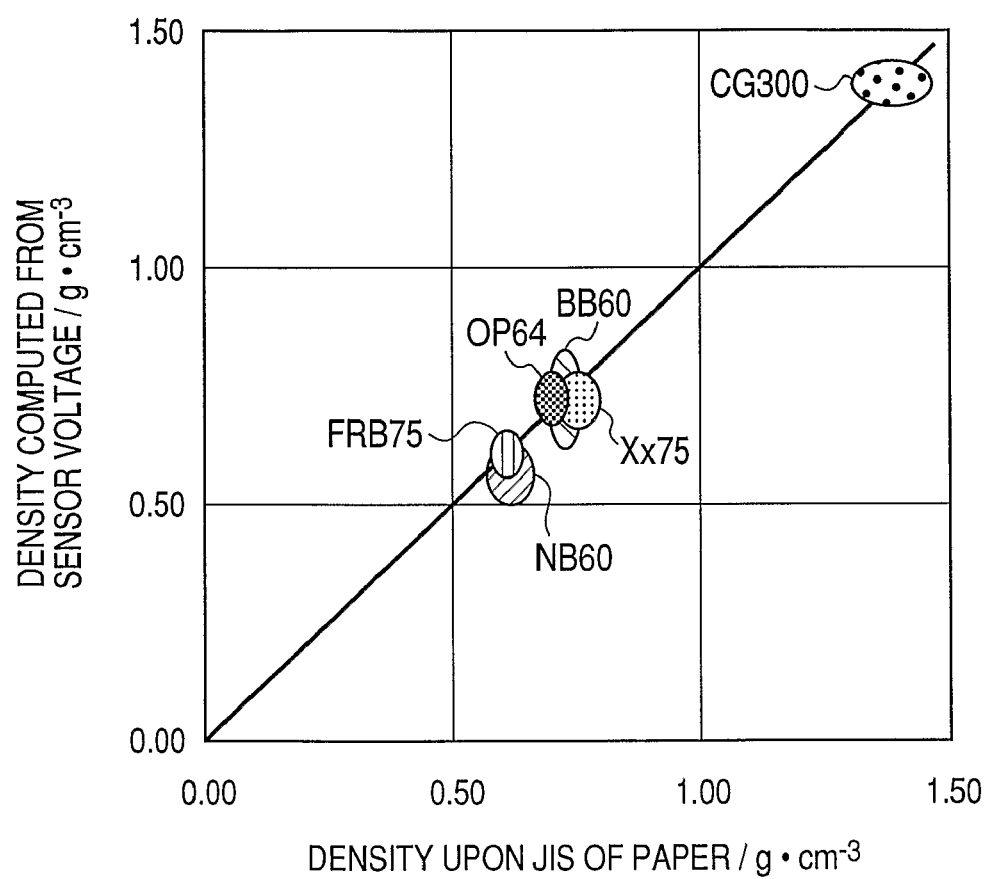
FIG. 7 illustrates the results of measurement in the present invention.

FIG. 6 illustrates comparison of the thicknesses computed from the above multiple regression equation with the thicknesses measured actually according to JIS standard. FIG. 7 illustrate comparison of the densities computed from the above multiple regression equation with the densities measured according to JIS standard. FIG. 6 and FIG. 7 show that the thicknesses and densities computed from the measurements of the present invention coincide with the thicknesses and densities measured according to JIS standard. Then the multiple regression equations (3) and (4) were memorized in the information memory unit.

Next, an unknown recording sheet was subjected to measurement. The two impacts generated the voltages of 3.81 volts and 0.95 volt. From the generated voltages and equations (3) and (4) memorized in the information memory unit, the unknown recording sheet were estimated to have a thickness of 0.099 mm and a density of 0.75 g/cm$^3$.

Example 2

Figure 8:
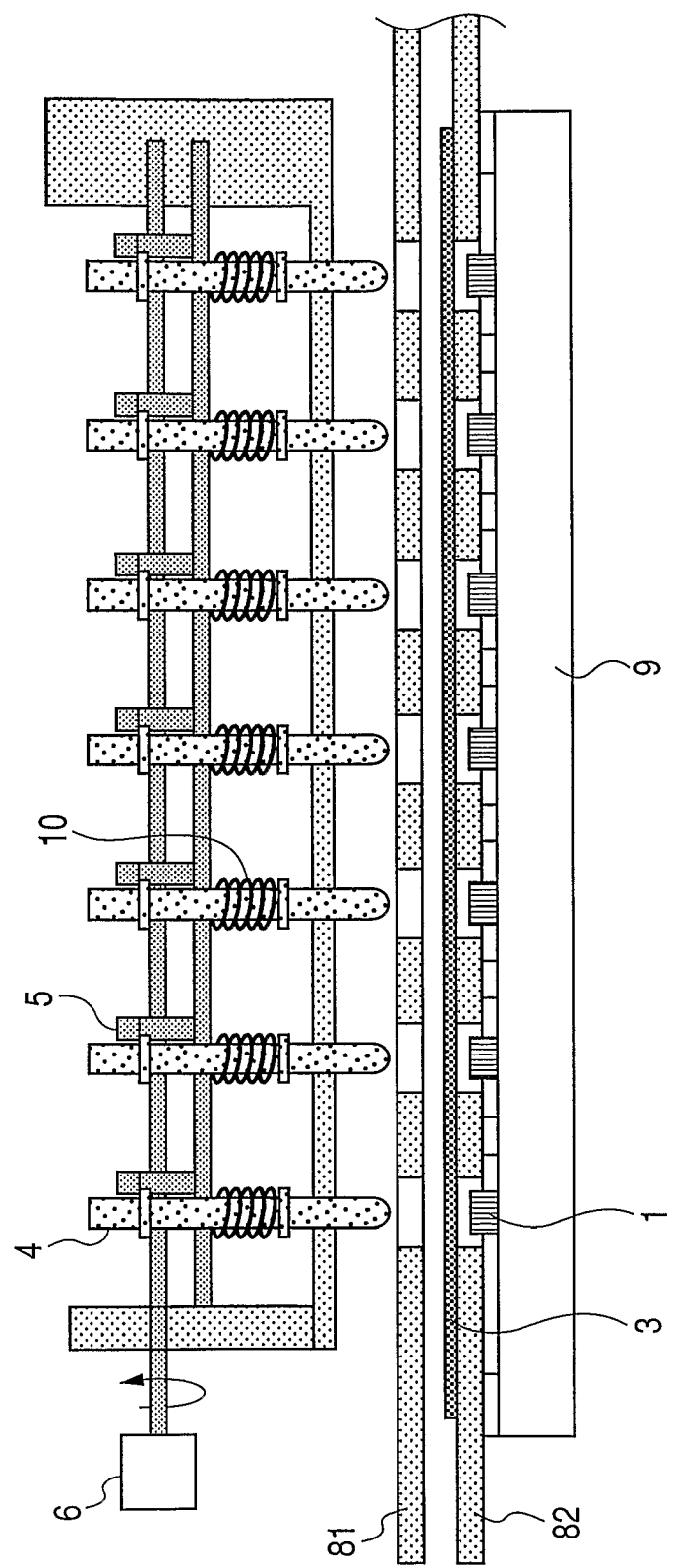
FIG. 8 illustrates schematically a principle of a constitution of the present invention.

FIG. 8 illustrates schematically a constitution of an impact-applying unit and a signal-detecting unit of the present invention. Measurement object 3 is a recording sheet used in copying machines and laser beam printers. Impact forces are applied to the measurement object by springs 10 and cams 5 rotated by motor 6. Cams 5, impact-applying members 4, and pressure sensors 1 are provided in seven sets, and are placed symmetrically along the direction of the long side of the A4-size sheet. Pressure sensors 1 are fixed to table 9. The impact-applying members are made of stainless steel and have respectively a diameter of 3.5 mm and a weight of 5.6 g. In FIG. 8, the two impact-applying members at the end sides are placed respectively to apply impact at the position of 1.5 cm inside from the paper sheet edge. The impact strength, impact cycle period, and the impact times of the impact applied to the measurement object are adjusted by the rotation speed of motor 6, the shape of cams 5, and strength of springs 10. In this Example, impact force is applied twice in 0.15 second. Guide plates 81, 82 guide measurement object 3 delivered from the front side to the back side in FIG. 8 by a delivery unit not shown in the drawing. The falling velocities of the impact-applying members are set at 0.42 m/s and 0.21 m/s without placing the paper sheet on guide plate 82. Pressure sensors are placed to be 0.3 mm lower than the upper face of guide plate 82.

As the measurement objects, were used electrophotographic recording sheets (OHT CG3300 of Canon K.K.; Office Planner OP64; Bajar Bond BB60; Zerox Xx75; Neena Bond NB60; and Fox River Bond FRB75). With the recording sheets, the multiple regression equations were derived by use of Excel® (spreadsheet software) of Microsoft Corporation installed in a personal computer containing an OS of Windows® 2000 of Microsoft Corporation. For comparison, the paper sheet thickness was measured by a paper thickness tester (Kumagaya Riki Kogyo K.K.: TM600) specified by JIS standard: The density of the paper sheet was calculated from the basis weight measured by weighing the A4-size paper sheet by an electronic balance and the paper sheet thickness measured by paper thickness tester TM600, as described by ENOMAE Toshiharu: Nippon Gazoh Gakkai-shi (Journal of Image Technology Society of Japan), vol. 43, (No. 4), 276 (2004), (P277).

When a paper sheet came to be delivered to the set position of the sensors, motor 5 was started to work to apply an external force to the paper sheet. With a paper sheet Xx75 as an example, the pressure sensor at the middle position gave an output pattern which is the same as that shown in FIG. 3.

With the paper sheet being delivered at a rate of 3.5 cm/min, seven impact-applying members 4 were driven simultaneously, and the measurement was conducted three times with one paper sheet. The same measurement was conducted with 30 paper sheets in total. From the entire measurement results, the multiple regression equations below were derived regarding the paper sheet thickness t (mm) and the paper sheet density $\rho$ (g/cm$^3$) as functions of the generated voltages $V_1$ (V) at the impact velocity of 0.42 m/s, and the generated voltage $V_2$ (V) at the impact velocity of 0.21 m/s. The correlation coefficients were respectively not less than 0.98 for the both multiple regression equations.

$$t = 1.04 \times 10^{-3} V_1 - 3.31 \times 10^{-2} V_2 + 0.131 \tag{5}$$

$$\rho = 0.148 V_1 - 0.129 V_2 + 0.310 \tag{6}$$

Multiple regression equations were also derived for each of seven impact-applying members 1-7. The multiple regression equations were different little: the dispersions of the coefficients and the constants were within 0.6%.

Next, the stiffness measured by a Gurley stiffness tester (Kumagaya Riki Kogyo K.K.: Automatic Gurley stiffness tester), and the density were processed for multiple regression. The multiple regression equation for the density was the same as Equation (6) above. The multiple regression equation for Gurley stiffness G (mgf) was obtained as below. The correlation coefficient thereof was 0.96.

$$G = 8.63 V_1 - 1.29 \times 10^2 V_2 + 1.77 \times 10^2 \tag{7}$$

Figure 9:
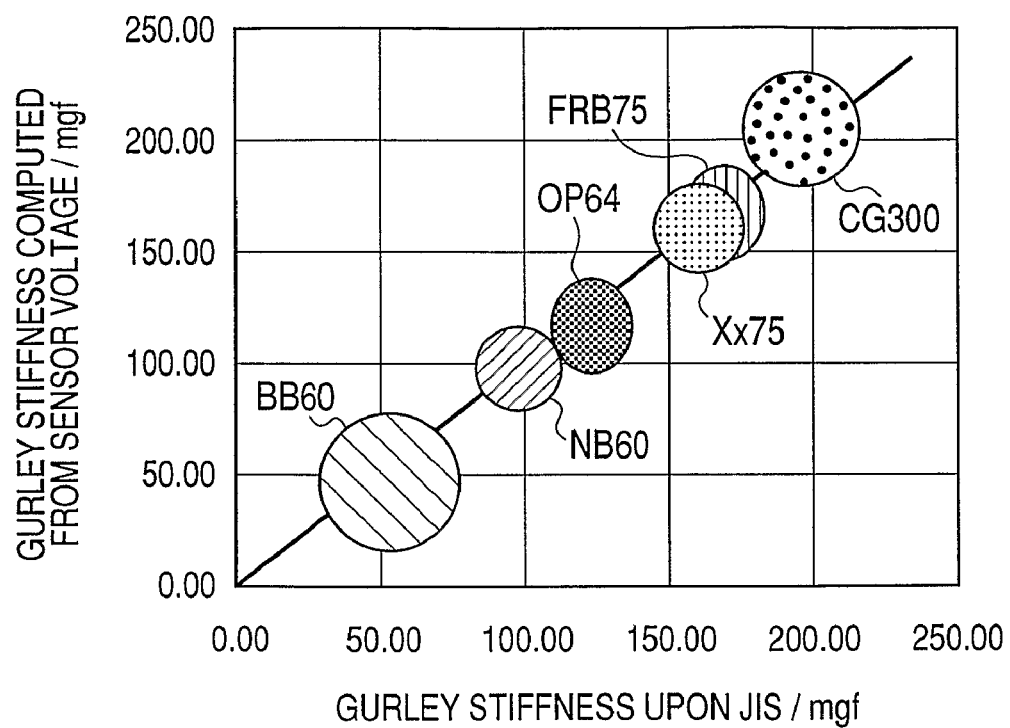
FIG. 9 illustrates the results of measurement in the present invention.

FIG. 9 is a graph showing the measured stiffness based on JIS standard on the abscissa and the calculated stiffness by multiple regression equation (7) on the ordinate. The Gurley stiffness estimated by the present invention corresponds well to the stiffness measured based on JIS standard. The dispersion of the measurement results of the present invention for the respective paper sheets is about the same level as that of the measurement based on JIS standard. Also, the results calculated by regression equations (5) and (6) correspond well to the measurement results based on JIS standard.

Ten sheets of Neena Bond 60 were subjected to measurement. In the measurement, the impact was applied twice at an impact velocity of 0.42 m/s and at an impact velocity of 0.21 m/s as one impact cycle. Onto each one paper sheet being delivered, three cycles of the impact were applied. Since the paper sheet was under delivery, the impacted positions were changed in every impact application on one paper sheet. Therefore the measurement was conducted on 21 positions on one paper sheet by use of seven impact-applying members. As the results, in the first paper sheet tested, the measured values at the 21 positions were scattered in a range of about 5%. This sheet of Neena Bond 60 had an average thickness of 0.101 mm, an average density of 0.60 g/cm$^3$, and an average Gurley stiffness of 99 mgf. From the result of the measurement, the paper sheet was relatively uniform in the density and thickness, and was flat with less distortion in the entire shape. Nearly the same results were obtained with the other nine sheets. For example, the average paper sheet thickness was respectively 0.099 mm, 0.100 mm, 0.098 mm, 0.102 mm, 0.101 mm, 0.099 mm, 0.101 mm, 0.101 mm, and 0.102 mm.

FIG. 10 illustrates the plots of the densities (on the ordinate) and the Gurley stiffness (on the abscissa) of the paper sheets calculated by multiple regression equations (6) and (7). In FIG. 10, the coordinate plane can be divided into three regions of A, B, and C by the dotted boundary lines for estimating the category of the paper sheet. Region A corresponds to OHT; region B corresponds to plain paper sheets; and region C corresponds to bond paper sheets. Finer division of the regions enables identification of the paper-type number. Therefore, the sensor of the present invention enables identification of not only the paper sheet thickness, paper sheet density, and Gurley stiffness, but also property distribution within the paper sheet for quality control, the category and paper-type number of the paper sheet.

Example 3

FIG. 4 illustrates a constitution of the sensor of the present invention. As illustrated in FIG. 4, the sensor is constituted of impact-applying unit 41, signal-detecting unit 42, signal-processing unit 43, signal-judging unit 44, information memory unit 45, and display unit 46. FIG. 5 illustrates constitution of impact-applying unit 41. A personal computer employing Windows® XP of Microsoft Corporation as OS is used for signal processing unit 43, signal-judging unit 44, information memory unit 45, and display unit 46. Excel® (spreadsheet software) of Microsoft Corporation is used for the statistical treatment. For comparison, the properties of the recording sheet are measured according to JIS standard. The density of the paper sheet is measured in a manner as described by ENOMAE Toshiharu: Nippon Gazoh Gakkai-shi (Journal of Image Technology Society of Japan) vol. 43, (No. 4), 276 (2004), (P277).

Plural recording sheets are used which have a thickness t (mm), a density $\rho$ (g/cm$^3$), a Gurley stiffness G (mgf), a moisture content H (g/cm$^2$) and a smoothness R ($\mu$m). An impact of $v_1$ (m/sec) generates a voltage $V_1$ (V), and an impact of $v_2$ (m/sec) generates a voltage $V_2$ (V). The measurement is conducted plural times with each paper sheet. Multiple regression equations (8), (9), (10), (11), and (12) are assumed, and the coefficients a, b, c, d, e, f, g, h, i, j, k, l, m, n, and o are determined by a least square method by utilizing the function of the aforementioned Excel.

$$t = aV_1 - bV_2 + c \tag{8}$$

$$\rho = dV_1 - eV_2 + f \tag{9}$$

$$G = gV_1 - hV_2 + i \quad (10)$$

$$H = jV_1 - kV_2 + l \quad (11)$$

$$R = mV_1 - nV_2 + o \quad (12)$$

The measurement results obtained by the measurement methods specified by JIS are compared with the calculation results obtained from the above regression equations, and the correlations are confirmed. Then the multiple regression equations are memorized together with the correlation coefficients of the multiple regression equations in the information memory unit. If the correlation coefficient between the value derived from the multiple regression equation and the value obtained by measurement according to JIS is lower than a predetermined level, one or more of the regression equations (8) to (12) are modified in the function form, and the coefficients are determined again. The predetermined correlation coefficients may be decided depending on the purpose. When the absolute values of properties or characteristics of the paper sheet should be considered, the correlation coefficients is preferably close to 1 (e.g., 0.9 or higher). However, for consideration of a magnitude relation, the correlation coefficient may be lower (e.g., about 0.7).

After memorization of the multiple regression equations, an unknown paper sheet is subject to the measurement, and the intended properties or characteristics are calculated from multiple regression equations (8), (9), (10), (11), and (12). Thus, plural properties or characteristics can be estimated by one observation (measurement of $V_1$ and $V_2$ in the present invention) with one sensor.

Further information which cannot be described by a numerical quantity, like a paper-type number and paper category, can be obtained by plotting the aforementioned value on a graph, or correlating it with another physical property. The information can be displayed on a display unit.

Example 4

Using each recording paper for electrophotography Xerox Xx75 on which each test pattern of color toners has been fixed respectively (hereinafter "paper to be tested"), measurements of thickness $\alpha$ (μm), toner thickness $\beta$ (μm) and smoothness R (μm) of the paper to be tested are explained in the following. FIG. 4 illustrates constitution of a sensor of the present invention. FIG. 5 illustrates constitution of impact-applying unit 41. A personal computer employing Windows® XP of Microsoft Corporation as OS is used for signal processing unit 43, signal-judging unit 44, information memory unit 45, and display unit 46. Excel® (spreadsheet software) of Microsoft Corporation is used for the statistical treatment. For comparison, the thickness and smoothness of the paper to be tested are measured according to JIS standard. The toner thicknesses are measured by a electron microscope.

An impact of $v_1$ (m/sec) generates a voltage $V_1$ (V), and an impact of $v_2$ (m/sec) generates a voltage $V_2$ (V). The measurement is conducted plural times with each paper to be tested. Multiple regression equations (13), (14) and (15) are assumed, and the coefficients p, q, r, s, t, u, w, x and y are determined by a least square method by utilizing the function of the aforementioned Excel.

$$\alpha = pV_1 - qV_2 + r \quad (13)$$

$$\beta = sV_1 - tV_2 + u \quad (14)$$

$$R = wV_1 - xV_2 + y \quad (15)$$

The relations among the measurement results obtained by the measurement methods specified by JIS, a toner thickness and the calculation results obtained from the above multiple regression equations are evaluated, and the correlations are confirmed. Then the multiple regression equations are memorized together with the correlation coefficients of the multiple regression equations in the information memory unit. If the correlation coefficient between the value derived from the multiple regression equation and the value obtained by measurement according to JIS is lower than a predetermined level, one or more of the multiple regression equations (13) to (15) are modified in the function form, and the coefficients are determined again. The predetermined correlation coefficients may be decided depending on the purpose. When the absolute values of properties or characteristics of the paper sheet should be considered, the correlation coefficients is preferably close to 1 (e.g., 0.9 or higher). However, for consideration of a magnitude relation, the correlation coefficient may be lower (e.g., about 0.7). The correlation may vary depending on the contents of explanation for determining the multiple regression equations such as the number of papers to be tested and the number of measurement in the present invention. When the correlation in another function form of the multiple regression equation is smaller than that established first, the desired correlation can be obtained by changing the number of measurement, the number of papers to be tested, varying the values of $v_1$ m/s and $v_2$ m/s.

After memorization of the multiple regression equations, the paper to be tested the toner thickness of which is unknown is subject to the measurement, and the intended properties or characteristics are calculated from multiple regression equations (13), (14) and (15). Thus, such plural kinds of properties as thickness, toner thickness and smoothness of the paper to be tested can be estimated by one observation (measurement of $V_1$ and $V_2$ in the present invention) with one sensor.

Effect of the Invention

According to the present invention, a single sensor can determine quantitatively a physical property caused by combination of plural properties or characteristics, and can judge the phenomenon or state without employing plural sensors based on different principles.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications Nos. 2006-278919, filed Oct. 12, 2006 and 2007-230405, filed Sep. 5, 2007, which are hereby incorporated by reference herein in their entirety.

The invention claimed is:

1. A multi-functional sensor for deriving information on a recording sheet material comprising an impact-applying unit for applying an external mechanical force onto the recording sheet material, a signal-detecting unit for detecting a signal of response of the recording sheet material to the external mechanical force, a signal-processing unit for processing the signal, and
a signal-judging unit for deriving a property of the recording sheet material by comparison of a signal from the signal-detecting unit or the signal processing unit with information memorized preliminarily;
wherein the signal-processing unit comprises a separation section for separating the signal from the signal-detecting unit into output signals on the properties of the recording sheet material, and a processing section for deriving, by statistical treatment, a correlation equation showing a correlation between the separated output signal and the properties of the recording sheet material.

2. The multi-functional sensor according to claim 1, wherein the correlation equation is derived preliminarily by regression analysis of results of measurement of the properties of the recording sheet material.

3. A method of detection of a state or phenomenon caused by combination of properties of a recording sheet material, comprising the steps of:

separating an output signal from a sensor into information on the properties, and deriving the property of the recording sheet material based on a correlation equation derived preliminarily by statistical processing on correlation between the separated output signal and the property of the recording sheet material.

4. The method of detection according to claim 3, wherein the correlation equation is derived preliminarily by regression analysis of results of measurement of properties of the recording sheet material.

5. The method of detection according to claim 3, wherein the property of the recording sheet material to be measured is at least one selected from the group consisting of mechanical properties, elastic properties, viscoelastic properties, properties relating to an interface and internal structure.

* * * * *